United States Patent
Zhang et al.

(10) Patent No.: US 7,374,781 B2
(45) Date of Patent: May 20, 2008

(54) SUSTAINED RELEASE FORMULATIONS CONTAINING ACETAMINOPHEN AND TRAMADOL

(76) Inventors: Shuyi Zhang, 1 Doric Ave., Parsippany, NJ (US) 07054; Jin Wang, 116 Union St., Cedar Grove, NJ (US) 07009

(*) Notice: Subject to any disclaimer, the term of this patent is extended or adjusted under 35 U.S.C. 154(b) by 699 days.

(21) Appl. No.: 10/664,451

(22) Filed: Sep. 20, 2003

(65) Prior Publication Data

US 2004/0131671 A1 Jul. 8, 2004

(51) Int. Cl.
*A61K 9/48* (2006.01)
*A61K 9/54* (2006.01)
*A61K 9/56* (2006.01)

(52) U.S. Cl. .................. 424/451; 424/457; 424/458; 424/459

(58) Field of Classification Search ............... None
See application file for complete search history.

(56) References Cited

U.S. PATENT DOCUMENTS 5,336,691 A * 8/1994 Raffa et al. ............... 514/629
6,375,957 B1 * 4/2002 Kaiko et al. ............... 424/400
6,491,949 B2 * 12/2002 Faour et al. ............... 424/473

* cited by examiner

*Primary Examiner*—S. Tran
(74) *Attorney, Agent, or Firm*—Joseph A. Fuchs; Rockey, Depke & Lyons, LLC

(57) ABSTRACT

A sustained release formulation as a unit dose contains 100 mg-1000 mg of Acetaminophen and 15 mg-150 mg of tramadol hydrochloride, which comprises of 1) an immediate release portion comprising of 25%-75% of the total effective amount of drug in the dosage form and 2) a sustained release portion comprising of a) 25%-75% of the total effective amount of drugs in the dosage form; b) 6%-50% of gelling polymers of the total formulation, and c) optionally an enteric coating at a level of 5%-40% of the total formulation. The set forth formulation dissolves 25%-60% of the total drug in the first hour, 50%-90% of the total drug in the first four hours and not less than 80% of the total drug in the first 12 hours using USP dissolution method II at 50 rpm.

9 Claims, No Drawings

SUSTAINED RELEASE FORMULATIONS CONTAINING ACETAMINOPHEN AND TRAMADOL

FIELD OF THE INVENTION

The present invention is directed to a sustained release formulation of Acetaminophen and tramadol. Particularly, this invention is related to a formulation and dissolution specifications from a sustained release dosage form of acetaminophen tramadol in connection with an improved dose segment for a better patient compliance.

BACKGROUND OF THE INVENTION

Acetaminophen with Codeine Phosphate (Tylenol® with Codeine) or Hydrocodone Bitartrate (Vicodin®) or Oxycodone (Tylox®) is commonly used analgesic drugs, indicated for the relief of moderate to moderately severe pain. Acetaminophen with Codeine or Hydrocodone combines the analgesic effects of a centrally acting analgesic, codeine or hydrocodone, with a peripherally analgesic, acetaminophen. Opioids have for many years been used as analgesics to treat severe pain. They, however, produce undesirable side effects and as a result cannot be given repeatedly or at high doses. The side effect problems are well documented in the literature (J. Jaffe and W. Martin in chapter 15, "The Pharmacological Basis of Therapeutics", editors L. Goodman and A. Gilman, 5th Edition, 245, 1975), which discloses that morphine and its congeners, e.g., codeine, hydrocodone and oxycodone, are opioid agonist analgesics that exhibit side effects such as respiratory depression, constipation, tolerance and abuse liability.

As alternatives to using opioids, non-opioids such as acetaminophen (APAP) and aspirin are used as analgesics. APAP, like aspirin, is not subject to the tolerance, addiction and toxicity of the opioid analgesics. However, APAP and aspirin are only useful in relieving pain of moderate intensity, whereas the opioid analgesics are useful in relieving more intense pain; See Woodbury, D. and Fingl, E. in "The Pharmacological Basis of Therapeutics", 5th Ed.; Goodman, L. and Gilman, A., Chapter 15, pages 325 (1975).

To reduce the side effect problems of opioids, opioids have been combined with other drugs including non-opioid analgesic agents, which lowers the amount of opioid needed to produce an equivalent degree of analgesia. It has been claimed that some of these combination products also have the advantage of producing a synergistic analgesic effect. For example, A. Takemori, Annals New York Acad. Sci., 281, 262 (1976) discloses that compositions including combinations of opioid analgesics with drugs other than analgesics exhibit a variety of effects, i.e., subadditive (inhibitory), additive or superadditive. R. Taber et al., J. Pharm. Expt. Thera., 169(1), 29 (1969) disclose that the combination of morphine and methadone, another opioid analgesic, exhibits an additive effect. U.S. Pat. No. 4,571,400 discloses that the combination of dihydrocodeine, an opioid analgesic, and ibuprofen, a non-opioid analgesic, provides superadditive effects when the components are within certain ratios. A. Pircio et al., Arch. Int. Pharmacodyn., 235, 116 (1978) report superadditive analgesia with a 1:125 mixture of butorphanol, another opioid analgesic, and acetaminophen (APAP), a non-opioid analgesic, whereas a 1:10 mixture did not show any statistically significant superadditive analgesia.

An immediate-release tablet composition comprising a tramadol material and acetaminophen, and its use, was invented (U.S. Pat. No. 5,336,691). The usual adult dosage is one or two tablets (Ultracet™) every four to six hours. The compositions are pharmacologically useful in treating pain and tussive conditions. The compositions are also subject to less opioid side-effects such as abuse liability, tolerance, constipation and respiratory depression.

The benefits of sustained release dosage forms are well documented. To reduce the dose segment and increase the patient compliance is one of the purposes with sustained release formulations. It has been reported that sustained release oral solid dosage forms of opioid analgesics are provided as multiparticulate systems which are bioavailable and which provide effective blood levels of the opioid analgesic for at least about 24 hours (see U.S. Pat. No. 6,294,195). Sustained release tablets for acetaminophen may be prepared using coated acetaminophen particles and uncoated acetaminophen particles to compress them to tablets providing a combination of immediate release and sustained release dosage forms (see U.S. Pat. No. 6,126,969). An acetaminophen-sustained release tablet or tablet layer is formed by making a wet granulation, using Povidone (PVP) in water or alcohol-water as the granulating fluid which is mixed with acetaminophen, hydroxyethyl cellulose, a wicking agent e.g. microcrystalline cellulose, then drying and milling the granulation and blending with dry powdered erosion promoter, e.g. pregelatinized starch, wicking agent, lubricant e.g. magnesium stearate and glidant e.g. silicon dioxide, and compressing the resultant granulation, which upon administration results in a slow release of the acetaminophen (see U.S. Pat. No. 4,820,522).

It has previously been known in the art that controlled release compositions of opioid analgesics such as morphine, hydromorphone or salts thereof could be prepared in a suitable matrix. For example, U.S. Pat. No. 4,990,341 (Goldie) describes hydromorphone compositions wherein the dissolution rate in vitro of the dosage form, when measured by the USP Paddle Method at 100 rpm in 900 ml aqueous buffer (pH between 1.6 and 7.2) at 37.degree. C., is between 12.5 and 42.5% (by wt) hydromorphone released after 1 hour, between 25 and 55% (by wt) released after 2 hours, between 45 and 75% (by wt) released after 4 hours and between 55 and 85% (by wt) released after 6 hours.

In the pharmaceutical market today, there are only sustained release dosage forms available for individual analgesic drugs, for example, oxycodone or acetaminophen.

SUMMARY OF THE INVENTION

A novelty of the present invention is the provision of a sustained release formulation, which contains both analgesic drugs, acetaminophen and tramadol.

It is an object of the present invention to provide a method for substantially improving the efficiency and quality of pain management.

It is another object of the present invention to provide a dissolution specification from a sustained release analgesic formulation containing acetaminophen and tramadol, which substantially improves the efficiency and quality of pain management.

It is another object of the present invention to provide a method and formulation(s), which substantially provide the clinical efficiency at least for 8 hours required to control pain in patients.

DETAILED DESCRIPTION OF THE PREFERRED EMBODIMENTS

The present invention contemplates sustained release formulation of acetaminophen combined with tramadol. The present invention provides a method for pain management with a sustained release formulation of acetaminophen combined with tramadol. The pain management requires immediate relief of pain and sustaining pain relief for a period time. This invention provides 25%-60% of the total drug released in the first hour in a gastric fluid, 50%-90% of the total drug released in the first four hours and not less than 80% of the total drug released in the first 12 hours in an intestinal fluid using USP dissolution method II at 50 rpm for sustaining the pain relief.

In a particularly preferred form of the invention, the formulation may be used to provide a depot drug form for controlled release of Acetaminophen and Tramadol containing pharmaceutical composition. However, the formulation is also useful in connection with a variety of other pharmaceutical or active compositions, including water soluble compositions, water sparingly soluble compositions and water insoluble compositions, and therefore the invention should not be considered as being limited by the exact composition and/or nature of the pharmaceutical or other active composition which is released under controlled conditions therefrom.

In a preferred form selected from tablets and capsules, the controlled release formulation of the invention comprises of 1) a portion of immediate release dosage containing 25%-70% of the total drugs of Acetaminophen and tramadol or salts thereof; 2) a portion of sustained release dosage containing 25%-75%, preferably i) 25%-75%, preferably 30%-75% of total drugs of Acetaminophen and tramadol or salts thereof; ii) gelling polymers as the drug release controlling agents, having a viscosity within the range of from about 60 to about 7,000,000 centipoises, and preferably from about 100 to about 100,000 centipoises, in a 2% by weight water solution at 25° C., as measured by a Brookfield LV viscometer; and iii) optionally a enteric coating material selected from copolymers of acrylic and methacrylic acid, cellulose acetate phthalate, cellulose phthalate hydroxy propyl methyl ether, polyvinyl acetate phthalate, hydroxypropyl methylcellulose acetate succinate, cellulose acetate trimellitate, or a shellac.

The active drug contents of Acetaminophen and Tramadol or salts thereof in the overall tablet formulation may preferably range from about 40% to about 85% by weight. The total amount of the gelling polymers in the overall formulation may preferably range from about 6% to about 50% by weight. The total amount of the enteric polymer in the overall tablet formulation may preferably range from about 5% to about 40% by weight.

Suitable gelling polymers include hydroxy propyl methylcellulose, hydroxypropyl ethylcellulose, hydroxypropyl cellulose, hydroxy ethylcellulose, methylcellulose, xantham gums, alginate salts, polyethylene oxide, carboxyvinyl polymer, and a salt of a carboxymethyl cellulose.

The dosage forms in this invention include tablets and capsules containing one form or combination of pellets, granules, powders and 2-12 of mini-tablets.

In the specific examples set forth below, three specific embodiments of the invention for releasing Acetaminophen and Tramadol are exemplified. These embodiments have been designated as Examples 1, 2, 3 and 4.

TABLE 1

Example 1.

| Ingredient | Immediate Release | Sustained Release |
| --- | --- | --- |
| 1 Acetaminophen | 200.0 mg | 300 mg |
| 2 Tramadol Hydrochloride | 20.0 mg | 30.0 mg |
| 3 Microcrystalline Cellulose | 50.4 mg | 8.8 mg |
| 4 Povidone K-90 | 19.2 mg | 17.6 mg |
| 5 Starch | 19.2 mg | — |
| 6 Croscarmellose Sodium | 4.8 mg | — |
| 7 Sodium Alginate (Keltone LV) | — | 35.2 mg |
| 8 Hydroxypropyl Methylcellulose (Methocel K4M) | — | 39.6 mg |
| 9 Colloidal Silicon Dioxide | 3.2 mg | 4.4 mg |
| 10 Magnesium Stearate | 3.2 mg | 4.4 mg |
| Total | 320.0 mg | 440.0 mg |

For portion of immediate release, mix the suitable amounts of items 1 through 6 listed in above formulation in a mixer such as a high shear mixer granulator or planetary mixer to obtain homogeneity. The mix is then granulated in water or other suitable granulation fluids and dried in a dryer. The dried granular mass is then milled and then items 9 and 10 are added for blending. The lubricated granular mass is then compressed into mini-tablets using a tablet press for individual tablet weight of 160 mg. The foregoing steps are conventional steps used in the tablet forming industry.

For a portion of sustained release, mix the suitable amounts of items 1 through 3 and 7 and 8 listed in above formulation in a mixer such as a high shear mixer granulator or planetary mixer to obtain homogeneity. The mix is then granulated in water or other suitable granulation fluids and dried in a dryer. The dried granular mass is then milled and then items 9 and 10 are added for blending. The lubricated granular mass is then compressed into mini-tablets using a tablet press for individual tablet weight of 220 mg. The foregoing steps are conventional steps used in the tablet forming industry.

The mini-tablets are encapsulated in a capsule containing 2 immediate release mini-tablets and 2 sustained release mini-tablets.

TABLE 2

Example 2.

| Ingredient | Immediate Release | Sustained Release |
| --- | --- | --- |
| 1 Acetaminophen | 250.0 mg | 250.0 mg |
| 2 Tramadol Hydrochloride | 25.0 mg | 25.0 mg |
| 3 Microcrystalline Cellulose | 36.4 mg | 37.8 mg |
| 4 Povidone K-90 | 18.0 mg | 13.8 mg |
| 5 Starch | 18.0 mg | — |
| 6 Croscarmellose Sodium | 5.4 mg | — |
| 7 Sodium Alginate (Keltone LV) | — | 36.8 mg |
| 8 Hydroxypropyl Methylcellulose (Methocel K4M) | — | 41.4 mg |
| 9 Colloidal Silicon Dioxide | 3.6 mg | 4.6 mg |
| 10 Magnesium Stearate | 3.6 mg | 4.6 mg |
| 11 Copolymer of Methacrylic Acid (Eudragit L30D) | — | 30.0 mg |
| 12 Talc | — | 11.4 mg |
| 13 Triethyl Citrate | — | 4.6 mg |
| 14 Purified Water | — | (80 mg) |
| Total | 360.0 mg | 460.0 mg |

For portion of immediate release, mix the suitable amounts of items 1 through 6 listed in above formulation in a mixer such as a high shear mixer granulator or planetary mixer to obtain homogeneity. The mix is then granulated in water or other suitable granulation fluids and dried in a dryer. The dried granular mass is then milled and then items 9 and 10 are added for blending. The lubricated granular mass is then compressed into mini-tablets using a tablet press for individual tablet weight of 180 mg. The foregoing steps are conventional steps used in the tablet forming industry.

For a portion of sustained release, mix the suitable amounts of items 1 through 4, 7 and 8 listed in above formulation in a mixer such as a high shear mixer granulator or planetary mixer to obtain homogeneity. The mix is then granulated in water or other suitable granulation fluids and dried in a dryer. The dried granular mass is then milled and then items 9 and 10 are added for blending. The lubricated granular mass is then compressed into mini-tablets using a tablet press for individual tablet weight of 207 mg. The tablets are coated with items 11 through 14 to target a weight gain of 13 mg. The foregoing steps are conventional steps used in the tablet forming industry.

The mini-tablets are encapsulated in a capsule containing 2 immediate release mini-tablets and 2 sustained release mini-tablets.

TABLE 3

Examples 3 and 4

| Ingredient | Example 3 | Example 4 |
|---|---|---|
| 1 Acetaminophen (Micronized) | 325.0 mg | 390.0 mg |
| 2 Tramadol Hydrochloride | 37.5 mg | 45.0 mg |
| 3 Microcrystalline Cellulose | 22.5 mg | 44.0 mg |
| 4 Povidone K-30 | 20.0 mg | 24.0 mg |
| 5 Hydroxypropyl Methylcellulose (Methocel K100LV) | 40.0 mg | 40.0 mg |
| 6 Hydroxypropyl Methylcellulose (Methocel K4M) | 45.0 mg | 45.0 mg |
| 7 Colloidal Silicon Dioxide | 5.0 mg | 6.0 mg |
| 8 Magnesium Stearate | 5.0 mg | 6.0 mg |
| 9 Copolymer of Methacrylic Acid (Eudragit L30D) | 32.5 mg | — |
| 10 Talc | 12.2 mg | — |
| 11 Triethyl Citrate | 5.3 mg | — |
| 12 Purified Water | (81 mg) | |
| 13 Acetaminophen (Micronized) | 325.0 mg | 260 mg |
| 14 Tramadol Hydrochloride | 37.5 mg | 30.0 mg |
| 15 Hydroxypropyl Methylcellulose (Methocel E5) | 17.5 mg | 10.0 mg |
| Total | 930.0 mg | 900.0 mg |

For Example 3 mix the suitable amounts of items 1 through 6 listed in above formulation in a mixer such as a high shear mixer granulator or planetary mixer to obtain homogeneity. The mix is then granulated in water or other suitable granulation fluids and dried in a dryer. The dried granular mass is then milled and then items 7 and 8 are added for blending. The lubricated granular mass is then compressed into tablets using a tablet press for individual tablet weight of 500 mg. The tablets are coated with items 9 through 12 to target a weight gain of 50 mg. After completion of 10% of enteric coating, continue to coat active drug on to the tablets using suspension of items 13 through 15. The final product may be coated with a conventional film coating.

For Example 4 mix the suitable amounts of items 1 through 6 listed in above formulation in a mixer such as a high shear mixer granulator or planetary mixer to obtain homogeneity. The mix is then granulated in water or other suitable granulation fluids and dried in a dryer. The dried granular mass is then milled and then items 7 and 8 are added for blending. The lubricated granular mass is then compressed into tablets using a tablet press for individual tablet weight of 600 mg. The tablets are coated with items 13 through 15 in a suspension to form an immediate release drug layer. The final product may be coated with a conventional film coating.

The dissolution testing is performed using USP apparatus II (Paddle Method) at 50 rpm for the first hour in a simulated gastric fluid and for the second hour and after in a simulated intestinal fluid. The drug release from the preferred formulations above is as follows:

TABLE 4

Percent Drug Released from Dosage Forms

| Time | Example 1 | | Example 2 | |
|---|---|---|---|---|
| (Hour) | Acetaminophen | Tramadol | Acetaminophen | Tramadol |
| 0 | 0 | 0 | 0 | 0 |
| 1 | 52.8 ± 3.9 | 55.0 ± 4.8 | 49.8 ± 5.6 | 50.8 ± 5.2 |
| 2 | 64.2 ± 4.8 | 67.1 ± 4.3 | 56.7 ± 6.0 | 61.9 ± 4.8 |
| 4 | 85.1 ± 4.0 | 88.4 ± 3.7 | 82.9 ± 4.8 | 83.6 ± 4.3 |
| 6 | 98.0 ± 3.1 | 97.9 ± 2.9 | 96.7 ± 3.9 | 96.2 ± 3.4 |
| 8 | 100.6 ± 2.2 | 100.0 ± 2.4 | 102.4 ± 2.5 | 99.8 ± 2.8 |

TABLE 5

Percent Drug Released from Dosage Forms

| Time | Example 3 | | Example 4 | |
|---|---|---|---|---|
| (Hour) | Acetaminophen | Tramadol | Acetaminophen | Tramadol |
| 0 | 0 | 0 | 0 | 0 |
| 1 | 49.6 ± 6.2 | 49.8 ± 5.5 | 53.1 ± 5.3 | 55.5 ± 4.5 |
| 2 | 65.5 ± 5.1 | 66.4 ± 4.6 | 68.2 ± 4.8 | 71.4 ± 4.2 |
| 4 | 82.8 ± 4.8 | 84.8 ± 3.7 | 89.0 ± 4.2 | 89.6 ± 4.0 |
| 6 | 97.1 ± 3.5 | 97.7 ± 2.5 | 98.1 ± 3.6 | 99.0 ± 3.1 |
| 8 | 101.3 ± 2.6 | 101.0 ± 2.3 | 100.7 ± 2.7 | 101.3 ± 2.6 |

We claim:

1. A capsule for sustained release of drugs including a combination of acetaminophen of from 100 mg to 1,000 mg and tramadol or its salts of from 15 mg to 150 mg comprising:
   1) an immediate release portion comprising 25%-75% of the total effective amount of the acetaminophen and tramadol in the form selected from pellets, beads, granules and mini-tablets;
   2) a sustained release portion comprising:
      a. 25%-75% of the total effective amount of the acetaminophen and tramadol in the form selected from pellets, beads, granules and mini-tablets; and
      b. a gelling polymer in an amount by weight of the capsule of 6% to 50% and; 3) the capsule releases 25%-60% of the acetaminophen and the tramadol in the first hour in a simulated gastric fluid dissolution media, 50%-90% of the acetaminophen and the tramadol in the first four hours and not less than 80% of the acetaminophen and the tramadol in the first 12 hours in a simulated intestinal fluid dissolution media using USP dissolution method II at 50 rpm.

2. The capsule of claim 1 wherein the gelling polymer is selected from the group consisting of hydroxy propyl methylcellulose, hydroxypropyl ethylcellulose, hydroxypropyl cellulose, hydroxy ethylcellulose, methylcellulose, xantham gums, alginate salts, polyethylene oxide, carboxyvinyl polymer, or a salt of a carboxymethyl cellulose, said gelling polymer having a viscosity within the range of from about 60 to about 7,000,000 centipoises in a 2% by weight water solution at 25 degree C., as measured by a Brookfield LV viscometer.

3. The capsule of claim 1 wherein the pellets, beads, granules and mini-tablets of the sustained release portion are coated with an enteric polymers selected from the group consisting of polyacrylate material, cellulose acetate phthalate, cellulose phthalate hydroxy propyl methyl ether, polyvinyl acetate phthalate, hydroxy propyl methyl cellulose acetate succinate, cellulose acetate trimellitate, or a shellac.

4. A tablet for sustained release of drugs including a combination of acetaminophen of from 100 mg to 1,000 mg and tramadol or its salt of from 15 mg to 150 mg comprising:
   1) a sustained release portion comprising:
      a. 25%-75% of the total effective amount of the acetaminophen and tramadol; and
      b. a gelling polymers in an amount by weight of the tablet from 6% to 50%;
   2) an immediate release portion comprising 25%-75% of the total effective amount of the acetaminophen and tramadol layered or compressed on the sustained release portion; and 3) the tablet releases 25%-60% of the acetaminophen and the tramadol in the first hour in a simulated gastric fluid dissolution media, 50%-90% of the acetaminophen and the tramadol in the first four hours and not less than 80% of the acetaminophen and the and the tramadol in the first four hours and not less than 80% of the acetaminophen and the tramadol in the first 12 hours in a simulated intestinal fluid dissolution media using USP dissolution method II at 50 rpm.

5. The tablet of claim 4 wherein the gelling polymer is selected from the group consisting of hydroxy propyl methylcellulose, hydroxypropyl ethylcellulose, hydroxypropyl cellulose, hydroxy ethylcellulose, methylcellulose, xantham gums, alginate salts, polyethylene oxide, carboxyvinyl polymer, or a salt of a carboxymethyl cellulose, said gelling polymer having a viscosity within the range of from about 60 to about 7,000,000 centipoises in a 2% by weight water solution at 25 degree C., as measured by a Brookfield LV viscometer.

6. The tablet of claim 4 further comprising a coating on the sustained release portion of an enteric polymer selected from the group consisting of polyacrylate material, cellulose acetate phthalate, cellulose phthalate hydroxy propyl methyl ether, polyvinyl acetate phthalate, hydroxy propyl methyl cellulose acetate succinate, cellulose acetate trimellitate, or a shellac.

7. A sustained release dosage form of drugs including a combination of acetaminophen and tramadol comprising:
   1) A sustained release portion comprising:
      a. 25%-75% of the total effective amount of the acetaminophen and tramadol; and
      b. 6% 50% of a gelling polymers of the dosage form
   2) An immediate release portion comprising 25%-75% of the acetaminophen and tramadol, layered or compressed on the sustained release portion; and 3) the dosage form releases 25%-60% of the acetaminophen and the tramadol in the first hour in a simulated gastric fluid dissolution media, 50%-90% of the acetaminophen and the tramadol in the first four hours and not less than 80% of the acetaminophen and the tramadol in the first 12 hours in a simulated intestinal fluid dissolution media using USP dissolution method II at 50 rpm.

8. The dosage form of claim 7 wherein the gelling polymer is selected from the group consisting of hydroxy propyl methylcellulose, hydroxypropyl ethylcellulose, hydroxypropyl cellulose, hydroxy ethylcellulose, methylcellulose, xantham gums, alginate salts, polyethylene oxide, carboxyvinyl polymer, or a salt of a carboxymethyl cellulose, said gelling polymer having a viscosity within the range of from about 60 to about 7,000,000 centipoises in a 2% by weight water solution at 25 degree C., as measured by a Brookfield LV viscometer.

9. The dosage form of claim 7 further comprising an enteric polymer coating on the sustained release portion, the enteric polymers being selected from the group consisting of polyacrylate material, cellulose acetate phthalate, cellulose phthalate hydroxy propyl methyl ether, polyvinyl acetate phthalate, hydroxy propyl methyl cellulose acetate succinate, cellulose acetate trimellitate, or a shellac.

* * * * *